United States Patent
Jue et al.

(10) Patent No.: US 12,287,291 B1
(45) Date of Patent: Apr. 29, 2025

(54) METHOD AND MINIATURIZED APPARATUS FOR RAMAN SPECTROSCOPY USING ROTATABLE DIFFRACTION GRATING AND SLIT

(71) Applicant: Apollon Inc., Cheongju-si (KR)

(72) Inventors: Miyeon Jue, Seoul (KR); Young Kyu Kim, Seoul (KR); Aram Hong, Seoul (KR)

(73) Assignee: Apollon Inc., Cheongju-si (KR)

( * ) Notice: Subject to any disclaimer, the term of this patent is extended or adjusted under 35 U.S.C. 154(b) by 0 days.

(21) Appl. No.: 18/930,957

(22) Filed: Oct. 29, 2024

(30) Foreign Application Priority Data

Dec. 7, 2023 (KR) .................. 10-2023-0176641

(51) Int. Cl.
*G01J 3/44* (2006.01)
*G01N 21/65* (2006.01)

(52) U.S. Cl.
CPC ..... *G01N 21/65* (2013.01); *G01N 2201/0221* (2013.01); *G01N 2201/025* (2013.01); *G01N 2201/126* (2013.01)

(58) Field of Classification Search
CPC .... G01N 21/65; G01J 3/44; G01J 3/18; G01J 3/12; G01J 3/10; G01J 3/04; G01J 2003/062; G01J 2003/063; G01J 2003/064; G01J 2003/05; G01J 2003/066
See application file for complete search history.

(56) References Cited

U.S. PATENT DOCUMENTS

| | | | | |
|---|---|---|---|---|
| 5,359,409 A | * | 10/1994 | Wildnauer | G01J 3/18 356/334 |
| 2006/0012786 A1 | * | 1/2006 | Goto | G01J 3/04 356/451 |
| 2009/0066934 A1 | * | 3/2009 | Gao | G01N 1/2273 356/417 |
| 2013/0265566 A1 | * | 10/2013 | Smith | G01N 21/359 356/402 |
| 2022/0196557 A1 | | 6/2022 | Zheng et al. | |

FOREIGN PATENT DOCUMENTS

| | | |
|---|---|---|
| JP | 2020-078543 A | 5/2020 |
| KR | 10-2018-0061959 A | 6/2018 |
| KR | 10-2020-0018177 A | 2/2020 |

* cited by examiner

*Primary Examiner* — Abdullahi Nur
(74) *Attorney, Agent, or Firm* — United One Law Group LLC; Kongsik Kim; Jhongwoo Peck

(57) ABSTRACT

A compact Raman spectroscopic analysis device includes a housing that forms an internal accommodation space therein, a light source unit that is disposed within the housing and irradiates light onto a subject, a light receiving unit that is disposed within the housing and receives light reflected or scattered from the subject to obtain a Raman spectrum, and a processor that is disposed within the housing and configured to analyze biological material of the subject based on a peak area value of a Raman spectrum range corresponding to the biological material. The light receiving unit includes a diffraction grating that reflects the reflected or scattered light, a slit through which the reflected light passes, and a light detector.

7 Claims, 8 Drawing Sheets

METHOD AND MINIATURIZED APPARATUS FOR RAMAN SPECTROSCOPY USING ROTATABLE DIFFRACTION GRATING AND SLIT

CROSS-REFERENCE TO RELATED APPLICATION(S)

This application claims priority from Korean Application No. 10-2023-0176641 filed Dec. 7, 2023, which is incorporated herein by reference in its entirety.

TECHNICAL FIELD

The present disclosure relates to a Raman spectroscopic analysis technique, and more particularly, to a Raman spectroscopic analysis method using rotatable diffraction grating and optical slit passage and a miniaturized device therefor.

RELATED ART

The content described below merely provides background information related to the present disclosure and does not constitute prior art.

A continuous blood glucose monitoring device is a medical device that has a sensor attached to a patient (or a non-patient person) for an extended period of time to measure the patient's blood sugar level over a given period of time, check the increase and decrease trends in blood sugar level, and provide information so that the patient can control their diet or decide when to inject medicinal preparations such as insulin.

For this reason, in order to provide more appropriate health care for diabetic patients, domestic and international diabetes and endocrine societies have revised their guidelines and are recommending the use of continuous blood glucose monitoring devices regardless of the type of diabetes.

Most continuous glucose monitoring devices that are currently available commercially and approved by the U.S. Food and Drug Administration (FDA) for medical purposes use a method in which a needle of a metering device is inserted into the patient's body, and the blood sugar level measured from the needle is read using another device such as a smartphone.

Existing continuous blood glucose monitoring devices, which measure blood glucose invasively using needles, are painful to attach and can cause side effects such as inflammatory reactions due to their invasive nature. Additionally, these devices cannot be used for extended periods exceeding, typically, 15 days. Therefore, to address these issues, there is a need for technology that can measure blood glucose level non-invasively.

Furthermore, there is a need for a method to obtain various biometric information other than blood sugar in a non-invasive manner, as well as a means to implement a device capable of obtaining such biometric information in a compact form factor.

SUMMARY

An aspect of the present disclosure is to provide miniaturizing the size of a Raman spectroscopic analysis device by using rotatable grating and slit passage.

The aspects of the present disclosure are not limited to those mentioned above, and other aspects will be clearly understood by those skilled in the art from the description below.

According to an aspect of the present disclosure, a compact and miniaturized Raman spectroscopic analysis device according to the present disclosure may include a housing that forms an internal accommodation space therein; a light source unit that is disposed within the housing and irradiates light onto a subject; a light receiving unit that is disposed within the housing and receives light reflected or scattered from the subject to obtain a Raman spectrum; and a processor that is disposed within the housing and configured to analyze biological material of the subject based on a peak area value of a Raman spectrum range corresponding to the biological material.

The light receiving unit may include a diffraction grating that reflects the reflected or scattered light, a slit through which the reflected light passes, and a light detector. The diffraction grating may be rotated by a driving unit to allow an amount of light and a wavelength band that reaches the light detector to be adjusted.

The driving unit may include a motor, a worm gear system including a worm coupled to the motor and a worm wheel, and a holder disposed on an upper portion of the worm gear system. The diffraction grating unit may be disposed on an upper portion of the holder and configured to be rotated.

The compact Raman spectroscopic analysis device may further include a reference light source within the housing such that a reference position for rotational operation of the diffraction grating may be established using the reference light source. The compact Raman spectroscopic analysis device may further include an actuator for adjusting a width of the slit under the control of the processor.

The processor may be configured to extract biological information of the subject based on a peak area value of a Raman spectrum range corresponding to at least one of glucose, protein, ketone, alcohol, caffeine, lactic acid, or fat.

The processor may be configured to, in response to the compact Raman signal analysis device starting operation or being worn on a user's body, perform calibration by controlling the light source unit and the light receiving unit.

When the calibration is performed, the processor may be configured to control the light source unit to output the light at a predetermined intensity during a predetermined time period, and set a light amount and an exposure time for the light source unit for measuring blood sugar based on a peak corresponding to a specific Raman transition value among the Raman spectrum acquired during the predetermined time period by the light receiving unit.

According to an aspect of the present disclosure, a Raman spectroscopic analysis method according to the present disclosure may include outputting, by a light source unit disposed in a housing that forms an internal accommodation space; obtaining, by a light receiving unit that includes a diffraction grating, a slit, and a light detector, a Raman signal of light reflected or scattered from the subject; and analyzing, by a processor, biological information of the subject based on the Raman signal obtained by the light receiving unit. The diffraction grating may be rotated by a driving unit to allow an amount of light and a wavelength band that reaches the light detector to be adjusted.

The driving unit may include a motor, a worm gear system including a worm coupled to the motor and a worm wheel, and a holder disposed on an upper portion of the worm gear system, and the diffraction grating may be disposed on an upper portion of the holder to as to be rotated.

The compact Raman spectroscopic analysis device may further include a reference light source within the housing such that a reference position for rotational operation of the diffraction grating may be established using the reference light source.

Further, a computer program stored in a non-transitory computer-readable recording medium may be provided to execute a method disclosed in the present disclosure.

Further, a non-transitory computer-readable recording medium that contains program instructions, which when executed cause a processor to perform a method disclosed in the present disclosure may be provided.

According to the present disclosure, the size of the Raman spectroscopic analysis device can be miniaturized due to the use of rotatable diffraction grating and a slit for the light to pass therethrough, thereby improving the user's convenience.

The effects of the present disclosure are not limited to those mentioned above, and other effects will be clearly understood by those skilled in the art from the description below.

DETAILED DESCRIPTION

Figure 1:
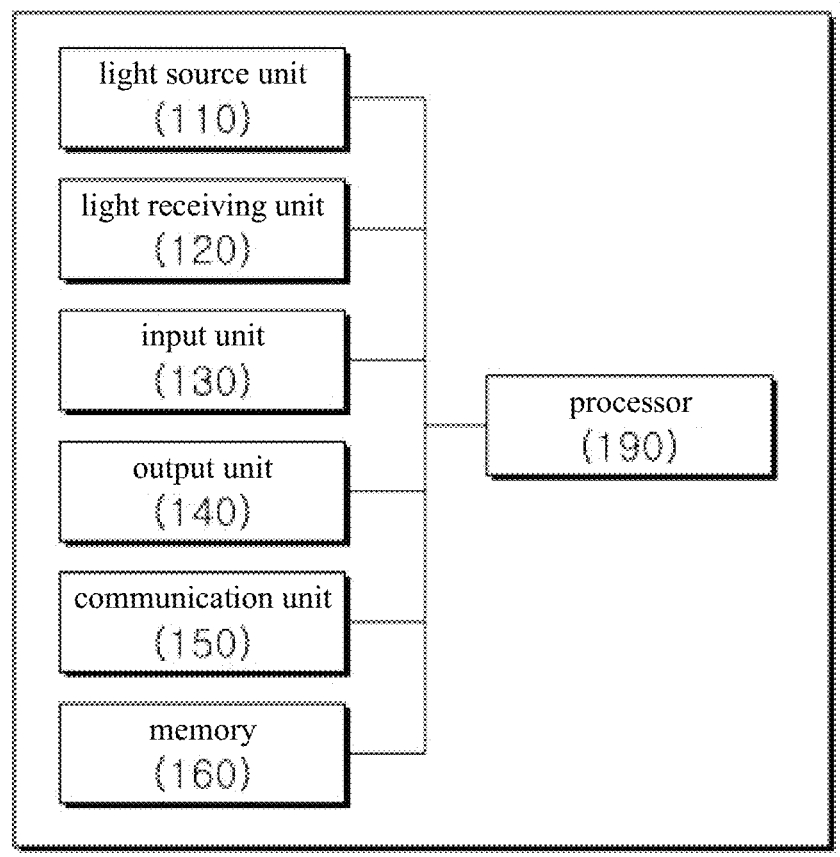
FIG. 1 is a block diagram illustrating the configuration of a Raman signal analysis device according to the present disclosure.

Throughout this disclosure, the same reference numerals denote the same components. The present disclosure may not describe all elements of the embodiments, and any content that is general in the technical field to which this disclosure belongs or that overlaps between embodiments may be omitted. The terms "unit," "module," "component," and "block" used in the specification can be implemented in software or hardware. Depending on the embodiments, a plurality of "units," "modules," "components," and "blocks" may be implemented as a single component, or a single "unit," "module," "component," and "block" may include a plurality of components.

Throughout the specification, when a part is said to be "connected" to another part, this includes not only cases where it is directly connected, but also cases where it is indirectly connected. The indirect connection may include a connection via a wireless communications network.

Also, when it is said that a part "comprises" or "includes" a component, it does not exclude the presence of other components unless specifically stated otherwise.

Throughout the specification, when an element is described as being disposed "on" another element, this includes not only the cases where the element is in contact with another element, but also the cases where one or more other elements exist between the two elements.

The terms "first," "second," and the like are used to merely distinguish one component from another and may not necessarily denote the order of components.

Singular expressions include plural expressions unless the context clearly indicates otherwise.

The reference numerals in each step are used for convenience of explanation and do not specify the order of the steps. Each step may be performed in a different order unless the context clearly indicates a specific sequence.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The operating principle and embodiments of the present disclosure are described below with reference to the attached drawings.

A miniaturized Raman spectroscopic analysis device according to the present disclosure may be implemented in various forms, including a wristwatch, wrist band, ring, belt, necklace, ankle band, thigh band, arm band, head band, or the like. However, the present disclosure is not limited thereto, and the miniaturized Raman spectroscopic analysis device according to the present disclosure may be implemented in any form that is suitable for attaching to the body.

FIG. 1 is a block diagram illustrating the configuration of a miniaturized Raman spectroscopic analysis device 100 according to the present disclosure.

Referring to FIG. 1, a miniaturized Raman spectroscopic analysis device (100) according to the present disclosure may include a light source unit 110, a light receiving unit 120, an input unit 130, an output unit 140, a communication unit 150, a memory 160, and a processor 190. However, the present disclosure is not limited thereto, and the continuous blood glucose measurement device according to the present disclosure may include more or fewer components than the above-described components. These components may be arranged inside a housing that forms an internal accommodation space therein. Hereinafter, each of the components will be described in detail.

The light source unit 110 may be configured to emit light so that light can reach a subject (e.g., skin of a user). To this end, the light source unit 110 may include at least one optical component from among a light source that outputs light, a lens that focuses the emitted light on one spot, an optical filter that filters out some wavelengths of the emitted light, a mirror that changes the direction in which the emitted light proceeds, and a beam splitter that reflects some portion of the light and transmits other portion of the light.

As described above, the light source unit 110 may include a light source and may include at least one optical component that changes at least one of the direction of propagation of the light, wavelength, polarization state, or light quantity until the light emitted from the light source reaches the subject.

Here, the light source unit 110 may be implemented as one or more light source units, and each light source unit 110 may output light of a different wavelength. The processor 190 may be configured to control each light source unit 110 to perform scheduling for light output.

The light receiving unit 120 may receive light reflected or scattered from the subject, and generate a Raman spectrum for Raman signal analysis. To this end, the light receiving unit 120 may include at least one of a lens that focuses light reflected or scattered from the subject to one point, an optical filter that filters out some wavelengths of light, a mirror that changes the direction in which light proceeds, or a diffraction member that disperses light by wavelengths to generate a spectrum of the light.

As described above, the light receiving unit 120 may include at least one configuration that changes at least one of the direction of propagation of the light, wavelength, polarization state, or light amount to generate a Raman spectrum by receiving light reflected or scattered from the subject, or generates a spectrum by dispersing the light by wavelengths.

Here, the light receiving unit 120 may be physically implemented as a plurality, and in this case, a beam splitter may be arranged on the light transmission path so that light may be received by each of the plurality of light receiving units 120.

In some embodiments, the light receiving unit 120 may be implemented as a single unit. In some other embodiments, the light receiving unit 120 may include an optical filter array, which includes a plurality of optical filters to obtain light reflected or scattered from the subject in various wavelength components, a micro lens array corresponding to the optical filter array, and an optical detection component array including a photo detection component corresponding to each of the optical filters. In other words, rather than physically including a plurality of light receiving units 120, the light receiving unit 120 may be implemented effectively as a plurality thereof by using an optical filter array, a micro lens array, and an optical detection component array.

The input unit 130 may receive information that is input from a user. When information is input through the input unit 130, the processor 190 may be configured to control the operation of the device to correspond to the input information. The input unit 130 may include a hardware physical key (for example, a button disposed on at least one of the front, rear, or side of the device, a dome switch, a jog wheel, a jog switch, or the like) and/or a software touch key. By way of an example, the touch key may be formed of a virtual key, a soft key, or a visual key displayed on a touch screen type display through software processing, or may be formed of a touch key placed on a part other than the touch screen. The virtual key or visual key may have various forms and be displayed on the touch screen, and may be formed of, for example, a graphic, a text, an icon, a video, or a combination thereof.

The output unit 140 may generate output associated with vision, hearing, or tactile sensations, and may include at least one of a display, an audio output device, a haptic module, or an optical output device.

The display may be implemented as a touch screen by forming a layered (e.g., laminated) structure or an integral structure with the touch sensor. The touch screen may function as a user input unit that provides an input interface between the device 100 and the user, and at the same time, may provide an output interface between the device and the user.

The audio output device may output audio data received through the communication unit or stored in the memory, or may output audio signals associated with functions performed by the device. The audio output device may include a receiver, a speaker, a buzzer, or the like.

The communication unit 150 may include one or more components that enable communication with an external device, and may include, for example, at least one of a wired communication module, a wireless communication module, or a short-range communication module.

The memory 160 may store data associated with various functions of the device 100 and a program for the operation of the processor 190. The memory 160 may store input/output data, application programs (or applications) that are run on the device 100, and data and commands for the operation of the device 100. At least some of these application programs may be downloadable from an external server via wireless communication. The memory 160 may be separately provided from the device. In some such embodiments, the memory 160 may include a database connected by wire or wirelessly.

The processor 190 may be implemented as a memory that stores data for an algorithm for controlling the operation of components within the device or a program to implement the algorithm, and at least one processor configured to perform the aforementioned operation based on the data stored in the memory. In some embodiments, the memory and the processor 190 may be implemented as separate chips. In some other embodiments, the memory and the processor 190 may be implemented as a single chip.

In addition, the processor 190 may be configured to control one or more of the components described above in combination, in order to implement on the device various embodiments according to the present disclosure to be described with reference to FIGS. 2-8 below.

Meanwhile, the function associated with artificial intelligence according to the present disclosure may be performed through a processor and a memory. The processor may be composed of one or more processors. As such, the one or more processors may be implemented as a general-purpose processor such as a CPU, an AP, a Digital Signal Processor (DSP), a graphics-only processor such as a GPU, a Vision Processing Unit (VPU), or an artificial intelligence-only processor such as an NPU. The one or more processors may be configured to control input data to be processed according to predefined operation rules or artificial intelligence models stored in the memory. Alternatively, when the one or more processors are implemented with artificial intelligence-only processors, they may be designed with a hardware structure specifically designed for processing a specific artificial intelligence model.

The predefined operation rules or artificial intelligence models may be created through learning. Here, being created through learning may mean that the basic artificial intelligence model learns by using a plurality of training data by a learning algorithm, thereby creating a predefined operation rules or artificial intelligence model configured to perform a desired characteristic (or purpose). Such learning may be performed in the device itself on which the artificial intelligence according to the present disclosure is performed, or may be performed through a separate server and/or system. Examples of the learning algorithm may include supervised learning, unsupervised learning, semi-supervised learning, or reinforcement learning. However, the present disclosure is not limited to the examples described above.

The artificial intelligence model may be composed of a plurality of neural network layers. The plurality of neural network layers may have a plurality of weight values, and may perform neural network operations through operations between the results of the previous layer and the plurality of weight values. The plurality of weight values of the plurality of neural network layers may be optimized by the learning results of the artificial intelligence model. For example, the plurality of weight values may be updated so that the loss value or cost value acquired from the artificial intelligence model is reduced or minimized during the learning process. The artificial neural network may include a deep neural network (DNN), and examples thereof include, but are not limited to, a convolutional neural network (CNN), a deep neural network (DNN), a recurrent neural network (RNN), a restricted boltzmann machine (RBM), a deep belief network (DBN), a bidirectional recurrent deep neural network (BRDNN), or deep Q-networks.

According to an exemplary embodiment of the present disclosure, a processor may be configured to implement artificial intelligence. Artificial intelligence refers to a machine learning method based on an artificial neural network that imitates human neurons (biological neurons) to enable a machine to learn. Artificial intelligence methodologies can be divided into supervised learning in which input data and output data are provided together as training data according to a learning method, so that an answer (output data) to a problem (input data) is determined, unsupervised learning in which only input data is provided without output data, so that an answer (output data) to a problem (input data) is not determined, and reinforcement learning in which learning is performed in a direction to maximize a reward, which is given from an external environment whenever an action is taken in a current state (State). In addition, artificial intelligence methodologies can be categorized by architecture, which represents the structure of the learning model. The architectures that are widely used in the deep learning technologies can be categorized into convolutional neural networks (CNNs), recurrent neural networks (RNNs), transformers, and generative adversarial networks (GANs).

The device may include an artificial intelligence model. The artificial intelligence model may be implemented as a single artificial intelligence model or may be implemented as a plurality of artificial intelligence models. Each of the one or more artificial intelligence models may be composed of a neural network (or an artificial neural network) and may include a statistical learning algorithm that mimics biological neurons in machine learning and cognitive science. A neural network may refer to a model in which artificial neurons (nodes) that form a network by combining synapses change the strength of the synapses through learning, thereby exhibiting a problem-solving ability. The neurons of the neural network may include a combination of weights or biases. The neural network may include one or more layers composed of one or more neurons or nodes. For example, the device may include an input layer, a hidden layer, and an output layer. The neural network constituting the device may infer a desired result (output) from an arbitrary input (input) by changing the weights of the neurons through learning.

Figure 2:
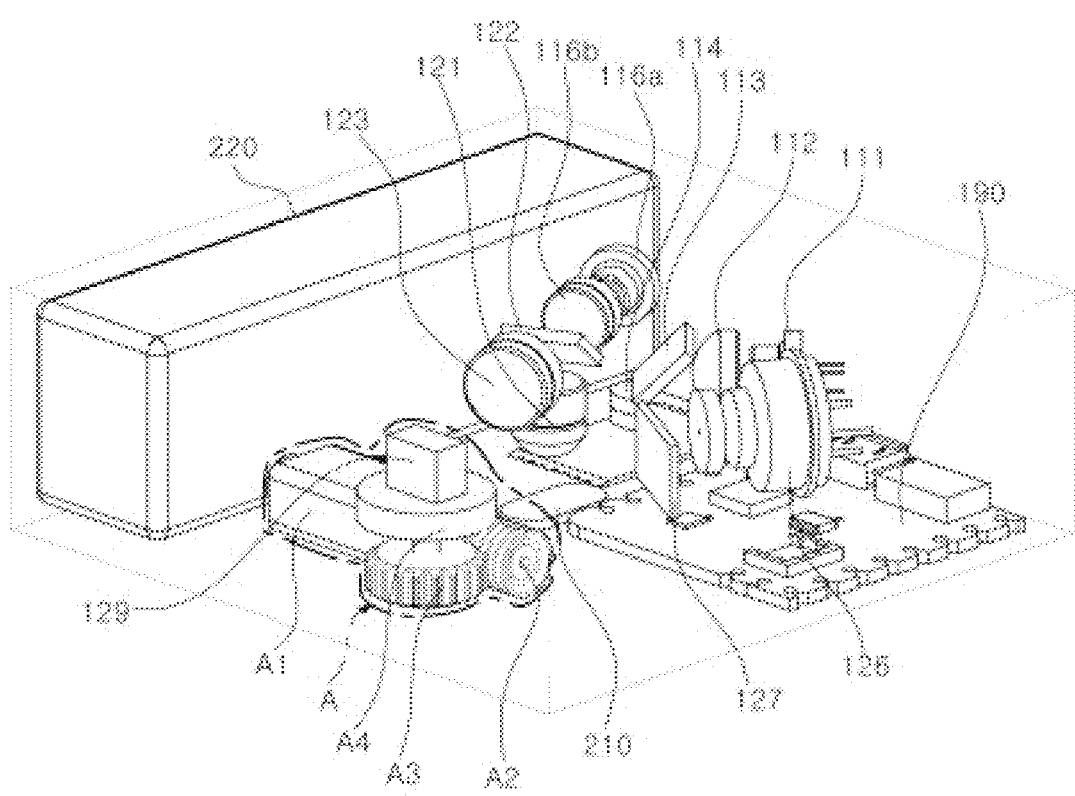
FIG. 2 is a perspective view illustrating the internal structure of a Raman signal analysis device including a plurality of light sources according to the present disclosure.
Figure 3:
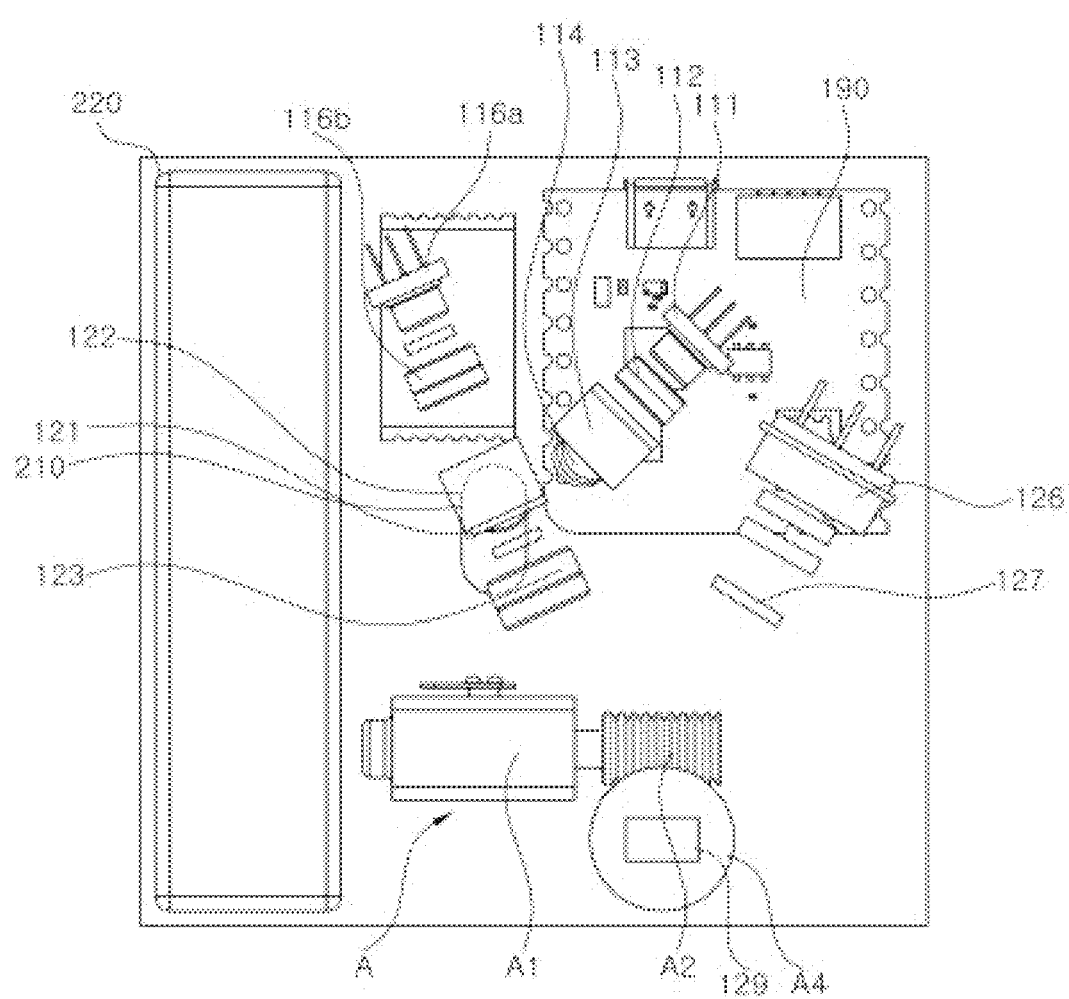
FIG. 3 is a plan view illustrating the internal structure of a Raman signal analysis device including a plurality of light sources according to the present disclosure.

FIG. 2 is a perspective view illustrating the internal structure of a compact Raman spectroscopic analysis device according to the present disclosure. FIG. 3 is a plan view illustrating the internal structure of a compact Raman spectroscopic analysis device according to the present disclosure. The components of the compact Raman spectroscopic analysis device 100 may be included inside a housing that forms an internal accommodation space therein.

Referring to FIGS. 2 and 3, a light source unit 110 may be disposed within the housing and may output light to a subject with a light source 111 included therein. For example, the light source 111 may irradiate near infrared rays (NIR) or mid infrared rays (MIR) to the subject. However, the wavelength emitted from the light source 111 may vary depending on the measurement purpose.

In some embodiments, the light source 111 may be implemented with a light emitting diode (LED) or a laser diode. However, the present disclosure is not limited thereto.

The light emitted from the light source 111 may pass through the first lens 112 and may be focused onto the first mirror 113. The first lens 112 may focus the light emitted from the light source 111 onto the first mirror 113. Accordingly, the first lens 112 may minimize battery consumption by eliminating the need to increase the output of the light source 111 above a certain level.

The light that passes through the first lens 112 may be reflected by the first mirror 113. The reflected light may pass through a narrow-band optical filter 114. The narrow-band optical filter 114 may be configured to increase the wavelength specificity of the light source.

The light that passes through the narrow-band optical filter 114 may be emitted to the exterior of the miniaturized Raman spectroscopic analysis device 100 through an aperture 210. Here, the aperture 210 may be formed on one side of the housing. For example, the housing may include a surface that may come into contact with the subject, when the device 100 is worn on the subject, and the light emitted from the light source 110 may be emitted to the exterior of the miniaturized Raman spectroscopic analysis device 100 through the contact surface.

A light receiving unit 120 may be disposed inside the housing and may obtain a Raman spectrum by receiving light reflected or scattered from the subject. The aperture 210 may be formed to allow the light reflected or scattered from the subject to return to the miniaturized Raman spectroscopic analysis device 100 therethrough.

When the miniaturized Raman spectroscopic analysis device 100 according to the present disclosure is mounted so that the contact surface thereof is in contact with the body, the light emitted to the exterior may reach the subject (e.g., skin).

The light that reaches the subject may be reflected or scattered and may enter the aperture 210. The light that enters the aperture 210 may pass through a long pass filter 121. The long pass filter 121 may block general reflected light and Rayleigh scattered light, which return from the subject, and may allow only the Raman scattering signal to pass through, thereby increasing the signal-to-noise ratio. The light that passes through the long pass filter 121 may be reflected by the second mirror 122.

In some embodiments, the light reflected from the second mirror 122 may pass through the optical filter 123. The optical filter 123 may allow only the light of a preset wavelength to pass through. Light that is not of the preset wavelength among the light incident on the optical filter 123 may be prevented from passing through the optical filter 123. The second mirror 122 may be implemented with a dichroic mirror and may reflect or transmit light of different wavelengths differently, so that the Raman scattered light and the reference light source 116a may reach the diffraction grating through the same optical path.

In some embodiments, the light that passes through the optical filter 123 may be collected through a second lens. The light collected through the second lens may be incident on a rotatable diffraction grating 129, and the light incident on the diffraction grating 129 may be divided into different wavelengths, pass through a slit 127, and subsequently be incident on the light detection unit 126.

Raman scattered light may be reflected by the diffraction grating 129. In particular, the light may be reflected at different reflection angles depending on the wavelength. Subsequently, only the light of a wavelength band selected by the slit 127 disposed in front of the light detector 126 may be incident on the light detector 126.

When the diffraction grating 129 is rotated, the positions of the wavelength bands of the dispersed Raman scattered light may change. Since the light detector 126 and the slit 127 are fixed, the wavelength band that reaches the light detector 126 also changes. In order to more accurately determine the wavelength band of the scattered light that reaches the light detector 126 by the rotation of the diffraction grating 129, a reference light source 116 having substantially the same optical path may be used. Accordingly, the detected wavelength band may be more accurately determined at a specific rotation position during the rotation of the diffraction grating 129.

The slit 127 may include a gap through which light is transmitted, and by adjusting the width of the slit, the amount of light that reaches the light detection unit 126 and the width of the wavelength band may be adjusted. In addition, a near-infrared absorbing material may be applied to the face of the slit to reduce optical interference within the device.

In some embodiments, an actuator for adjusting the width of the slit 127 may be included in the device 100. The processor 190 disposed within the housing may be configured to analyze the biological material based on a peak area value of the Raman spectrum range for the particular biological material of the subject. As the width of the slit increases, the amount of light reaching the light detection unit 126 increases, thereby increasing the signal. However, the wavelength resolution of the signal may be reduced due to the broad wavelength band being input to the light detection unit 126.

The light receiving unit 120 may include the diffraction grating 129 that reflects the light that has been reflected or scattered by the subject, the slit 127 through which the reflected light passes, and the light detection unit 126. The diffraction grating 129 may be rotated by a driving unit A to allow the amount and wavelength band of the light that reaches the light detection unit 126 to be adjusted.

The driving unit A may include a motor A1 (for example, a step motor), a worm gear mechanism including a worm A2, which is connected to the motor A1, and a worm wheel A3, and a holder A4 disposed on the upper part of the worm wheel A3. The diffraction grating 129 may be disposed on the upper part of the holder A4 so that it may be rotated. In some embodiments, a miniaturized actuator, a piezo actuator, or the like may be used instead of the motor, and various gear mechanisms, other than the worm gear, may be applied.

The light detection unit 126 may receive the light diffracted by the diffraction grating 129 and transmitted through the slit 127. The light detection unit 126 may convert the received light into an electric signal representative of the received light. The processor 190 may be configured to generate a Raman spectrum based on the electric signal. For example, the light detection unit 126 may be implemented as a Charge Coupled Device (CCD), an avalanche photodiode (APD) array, a photodiode (PD), and/or a complementary metal-oxide-semiconductor (CMOS). However, the present disclosure is not limited thereto.

Figure 4:
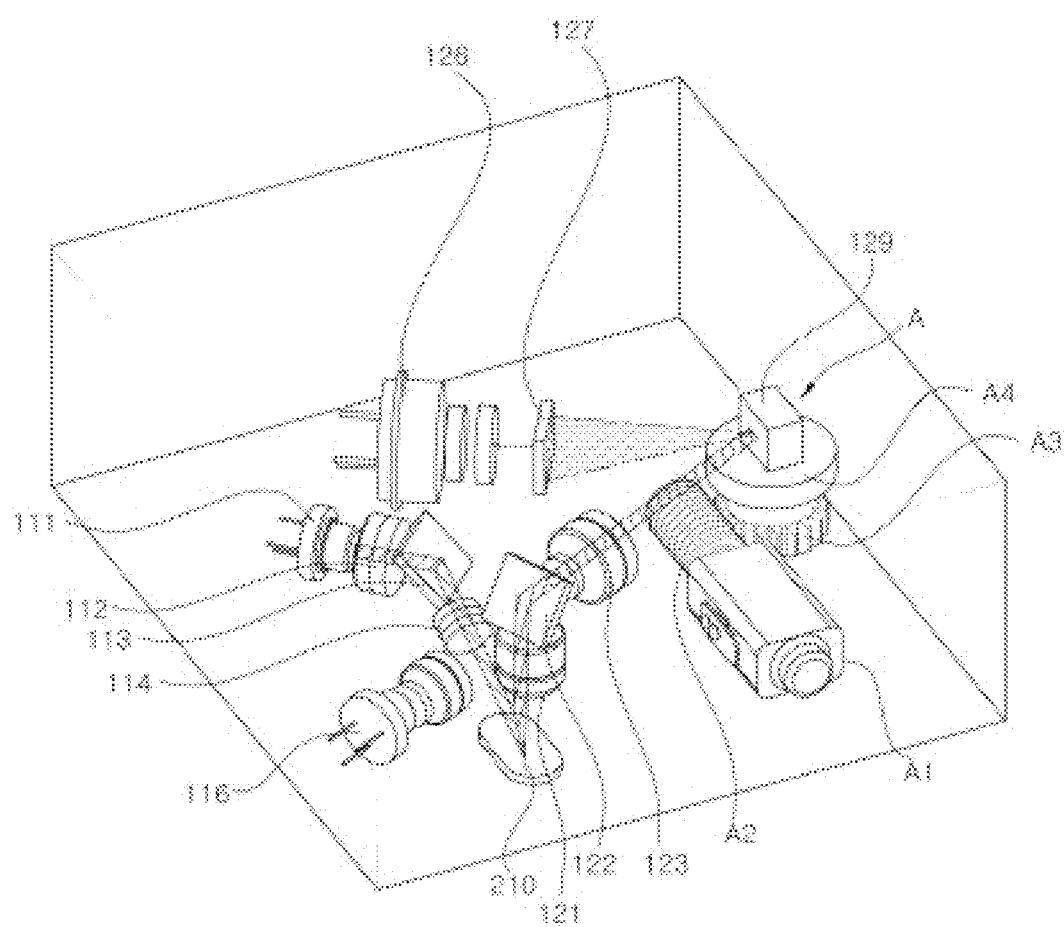
FIGS. 4 and 5 are drawings depicting the direction of light propagation due to the rotation of a diffraction grating arranged in a compact Raman spectroscopic analysis device according to the present disclosure.
Figure 5:
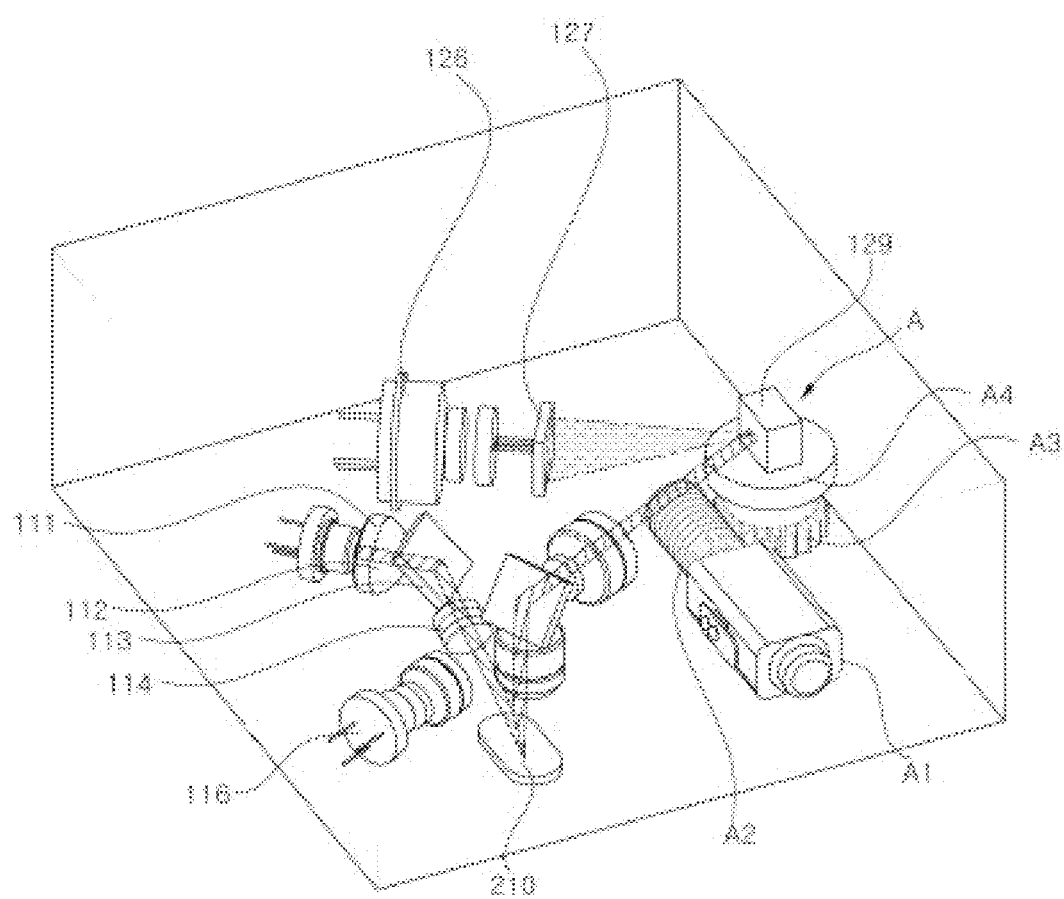

FIGS. 4 and 5 are drawings depicting the direction of light propagation due to the rotation of the diffraction grating disposed in the miniaturized Raman spectroscopic analysis device 100 according to the present disclosure.

The processor 190 may be configured to control the amount of light and the wavelength band of the light incident on the light detection unit 126 by controlling the width of the optical slit 127 using the driving unit A and the actuator. In other words, the processor 190 may be configured to cause the diffraction grating 129 to be rotated by controlling the driving unit A and the actuator that is provided for controlling the width of the optical slit 127.

As described above, the driving unit A may include a motor A1, a worm gear system including a worm A2 connected to the motor and a worm wheel A3, and a holder A4 disposed on top of the worm wheel A3. The diffraction grating 129 may be disposed on top of the holder A4 so as to be rotated thereby.

In some embodiments, the processor 190 may be configured to generate a Raman spectrum based on the signal generated from the light detection unit 126. The Raman spectrum may be generated so that it may be represented as a graph in which the x-axis is a Raman shift value (unit: $cm^{-1}$) and the y-axis is a signal intensity.

The processor 190 may be configured to measure the blood sugar level of the subject by analyzing the generated Raman spectrum. Prior to measuring the blood sugar level of the subject, the processor 190 may be configured to perform a calibration process for the Raman spectra specific to the blood sugar and skin proteins.

In some embodiments, during the calibration, the processor 190 may be configured to reduce noise in the generated spectrum through Savitzky-Golay filtering and to remove the background of the generated spectrum through polynomial fitting. The order of the polynomial fitting that is suitable for background removal may be determined based on the intensities of four wavelengths: namely, the initial wavelength, the wavelength at the two-quarter point, the wavelength at the three-quarter point, and the end wavelength.

Re-calibration may be performed when the processor 190 of the device is started, blood glucose measurement is stopped and then restarted, or the device is temporarily removed and then re-worn.

In some embodiments, when the device starts operating or is re-worn, the processor 190 may be configured to control the light source unit to output light at a predetermined output for a predetermined period of time. Subsequently, based on a peak corresponding to a predetermined Raman transition value among the Raman spectrum acquired for the predetermined period of time by the light receiving unit, the processor 190 may be configured to set the light amount and exposure time of the light source unit to be used for measuring blood sugar.

Herein, the Raman signal intensity corresponding to the predetermined Raman transition value may be a peak at about 1450 $cm^{-1}$.

During the calibration, if the Raman signal intensity corresponding to the predetermined Raman transition value does not reach the reference value even with the maximum output and maximum exposure time of the light source unit, the processor 190 may be configured to control the communication unit so that an error message is transmitted to an external terminal.

A user may check the error message through the external terminal connected to the miniaturized Raman spectroscopic analysis device 100 according to the present disclosure. The error message may include text or an image requesting a change of the attachment site or re-attachment of the device 100.

Meanwhile, if the intensity ratios of the acquired Raman signal picks differ from the intensity ratios of general Raman signal peaks by a predetermined threshold or more, the processor 190 may be configured to determine that there is poor contact between the subject and the device, and to control the communication unit 150 to transmit an error message to the external terminal.

However, without being limited thereto, the processor 190 may be configured to display an error message through the output unit 140 included in the continuous blood glucose measurement device 100, rather than transmitting the aforementioned error message to an external terminal.

Thereafter, the processor 190 may be configured to utilize machine learning techniques such as partial least squares (PLS), support vector machine (SVM), or deep learning using autoencoder, ResNet, or the like to correlate the peak area corresponding to each of glucose, protein, ketone, alcohol, caffeine, lactic acid, fat, or the like with the glucose level at the time of measurement. Accordingly, blood sugar of the subject may be continuously measured based on the learned model.

In some embodiments, the glucose level may be measured through a method such as finger prick, venous blood prick, and continuous CGM. However, the method of measuring the glucose level is not limited thereto.

In some embodiments, the processor 190 may be configured to estimate the amount of glucose in the interstitial fluid based on the ratio of the area of the peak having a center value of about 1450 $cm^{-1}$ to the area of the peak having a center value of about 1660 $cm^{-1}$ and the area of the peak having a center value of about 1125 $cm^{-1}$.

Herein, for the peak with a center value of about 1450 $cm^{-1}$, which corresponds to protein, the area may be calculated using the range of 1415 $cm^{-1}$ to 1480 $cm^{-1}$.

Further, for the peak with a center value of about 1660 $cm^{-1}$, which corresponds to fat, the area may be calculated using the range of 1630 $cm^{-1}$ to 1685 $cm^{-1}$.

Further, for the peak with a center value of about 1125 $cm^{-1}$, which corresponds to glucose, the area may be obtained using three ranges, namely, 1089 $cm^{-1}$ to 1160 $cm^{-1}$ (first range), 1115 $cm^{-1}$ to 1140 $cm^{-1}$ (second range), and 1120 $cm^{-1}$ to 1130 $cm^{-1}$ (third range).

In some embodiments, the processor 190 may be configured to obtain an area corresponding to ketone by using a range of $1700^{-1}$ to 1750 $cm^{-1}$ for the peak with a center value of about 1725 $cm^{-1}$, which corresponds to ketone.

In some embodiments, the processor 190 may be configured to obtain an area corresponding to alcohol by using a range of 1180 $cm^{-1}$ to 1220 $cm^{-1}$ for the peak with a center value of about 1200 $cm^{-1}$, which corresponds to alcohol.

In some embodiments, the processor 190 may be configured to obtain an area corresponding to the carbon-oxygen double bond of caffeine (i.e., carbonyl group of a caffeine molecule) by using a range of 1600 $cm^{-1}$ to 1700 $cm^{-1}$ for the peak with a center value of about 1650 $cm^{-1}$.

In some embodiments, for lactic acid, the processor 190 may be configured to obtain an area corresponding to the carboxyl group by using a range of 1700 $cm^{-1}$ to 1750 $cm^{-1}$ for the peak with a center value of about 1725 $cm^{-1}$.

As described above, the miniaturized Raman spectroscopic analysis device 100 according to the present disclosure may measure bio-information non-invasively, resulting in significantly fewer side effects compared to existing devices that require needle injection.

In some embodiments, the processor 190 may be configured to obtain all Raman scattering signal spectra within a specific range via the rotation of monochromatic light using the diffraction grating 129 and the slit 127, thereby allowing more accurate Raman signal spectrum measurement and analysis to be performed.

Figure 6:
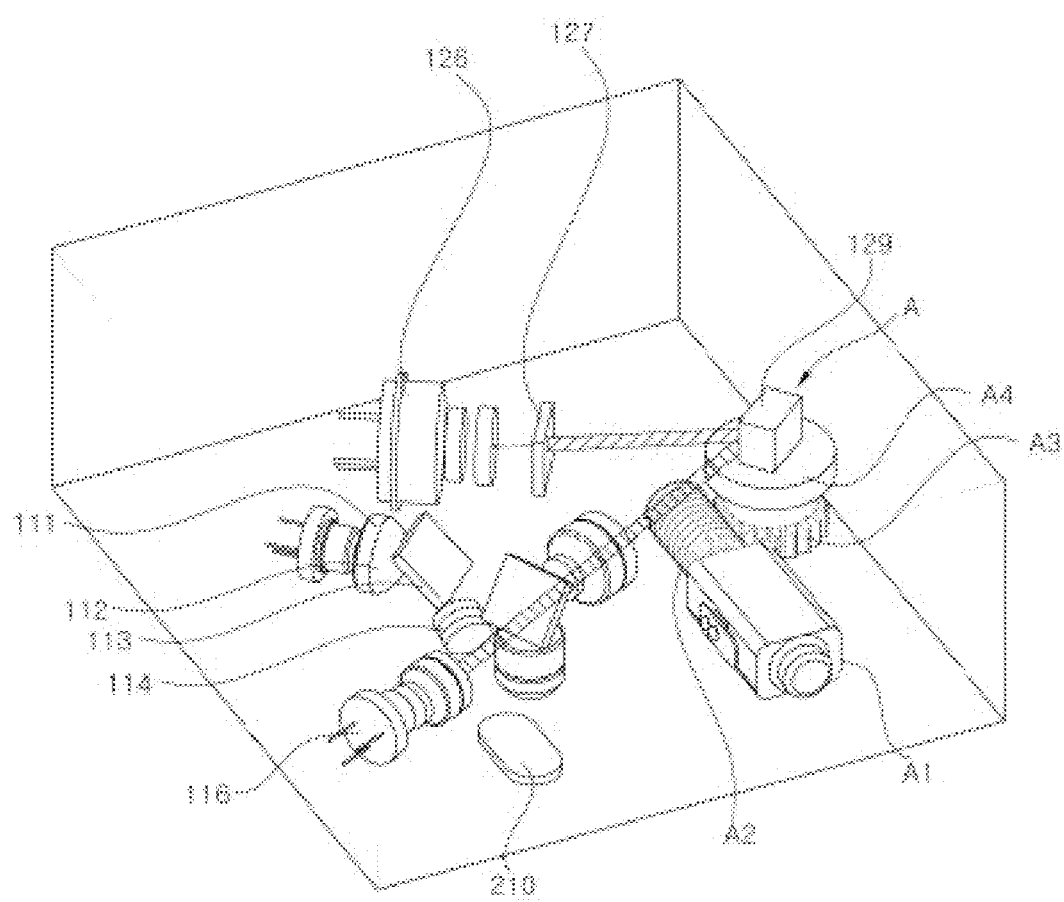
FIG. 6 is a drawing depicting the control of rotational motion of a diffraction grating using a reference light source in a compact Raman spectroscopic analysis device according to the present disclosure.

FIG. 6 is a drawing depicting the control of rotational motion of the diffraction grating using a reference light source 116 in the miniaturized Raman spectroscopic analysis device 100 according to the present disclosure.

The miniaturized Raman spectroscopic analysis device 100 according to the present disclosure may further include a reference light source 116 disposed inside the housing. Using the reference light source 116, a reference for rotational motion of the diffraction grating may be established.

The reference light source 116 may be added to the configuration to improve the operation accuracy for the diffraction grating 129, and the reference light source 116 may use the minimum band (e.g., the shortest wavelength) among the wavelength bands to be utilized. The rotational (e.g., angular) position of the diffraction grating 129 that allows the signal of the reference light source to be detected by the light detection unit 126 may be set as the reference angular position. Accordingly, the accuracy of the rotational operation of the diffraction grating 129 may be improved. In embodiments where the reference light source 116 is omitted, the angular position of the rotation axis of the diffraction grating 129 and the corresponding wavelength of light that is incident on the light detection unit 126 may be estimated by using the rotation control function of the step motor or the physical limit for further rotation and rotational speed.

Further, the miniaturized Raman spectroscopic analysis device 100 according to the present disclosure may include a battery 220 for powering the above-described components.

As described above, the miniaturized Raman spectroscopic analysis device 100 according to the present disclosure may measure blood sugar (and other various bio-information) continuously in a non-invasive manner, and therefore may present significantly fewer side effects compared to existing continuous blood sugar measurement devices that require needle injection.

In the conventional design of spectrometers for generating Raman spectra, an aperture is typically disposed at an outer corner rather than the center of the device to ensure a stable optical path for securing the light dispersion angle of a monochromator.

However, according to the present disclosure, the aperture 210 may be disposed at or near the center of the main body. In the case of a wearable device to be attached to the body, the main body and the user's body may be separated due to the user's activity. Since the center of the main body of the wearable device is likely to make the strongest contact with the user's body, the distance between the light source and the subject may be stably maintained as the aperture is disposed at the center of the contact surface of the housing.

To this end, according to the present disclosure, the aperture may be disposed substantially at the center of the contact surface included in the housing, and the light detection unit 126 and an internal battery 220 may be disposed at the outermost part inside the main body. The light source may be disposed so as to face the aperture 210 disposed at the center of the contact surface. Accordingly, the angle formed between the path of light incident from the light source to the first mirror and the path of light incident to the diffraction grating 129 may be greater than 90 degrees. However, the present disclosure is not limited thereto.

As a result, the miniaturized Raman spectroscopic analysis device 100 according to the present disclosure may experience problems such as a narrow measurement wavelength band due to insufficient light dispersion angle and optical path. The present disclosure solves the problem of the narrow measurement wavelength band by selectively analyzing only the blood sugar-specific wavelength band.

Due to such a configuration, the present disclosure enables the aperture to be disposed substantially at the center of the subject contact surface provided in the housing.

As described above, according to the present disclosure, the accuracy of blood sugar measurement may be improved by positioning the aperture through which the light to be irradiated to the subject is emitted at the center of the device. Further, the present disclosure may allow battery replacement without terminating or interrupting the blood sugar measurement.

Figure 7:
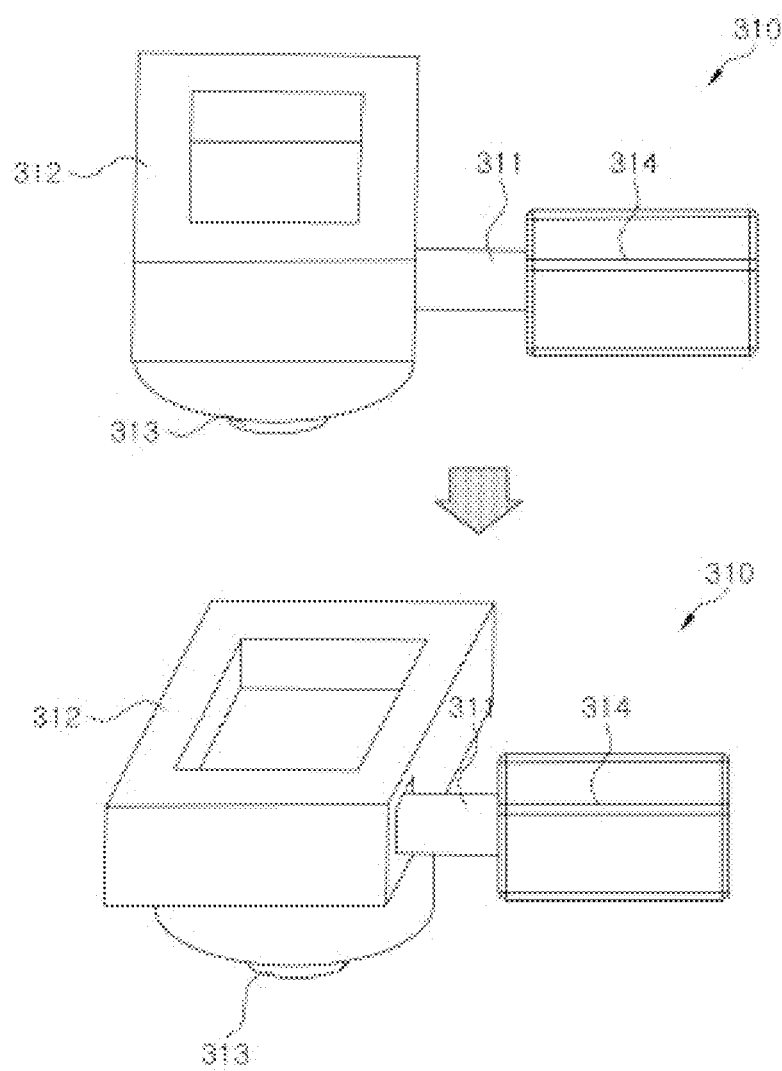
FIG. 7 is a drawing depicting a driving unit of a diffraction grating arranged in a compact Raman spectroscopic analysis device according to the present disclosure.

FIG. 7 is a drawing depicting the driving unit of the diffraction grating disposed in the miniaturized Raman spectroscopic analysis device 100 according to the present disclosure.

Due to the operation of the motor 314, a pushrod 311 extended to the motor 314 may move linearly, and a rotary plate 312 may be rotated due to the linear movement of the pushrod 311. The diffraction grating disposed above or below the rotary plate 312 may perform diffraction while being rotated. Instead of the motor 314, a linear actuator or a piezo actuator may also be used.

Figure 8:
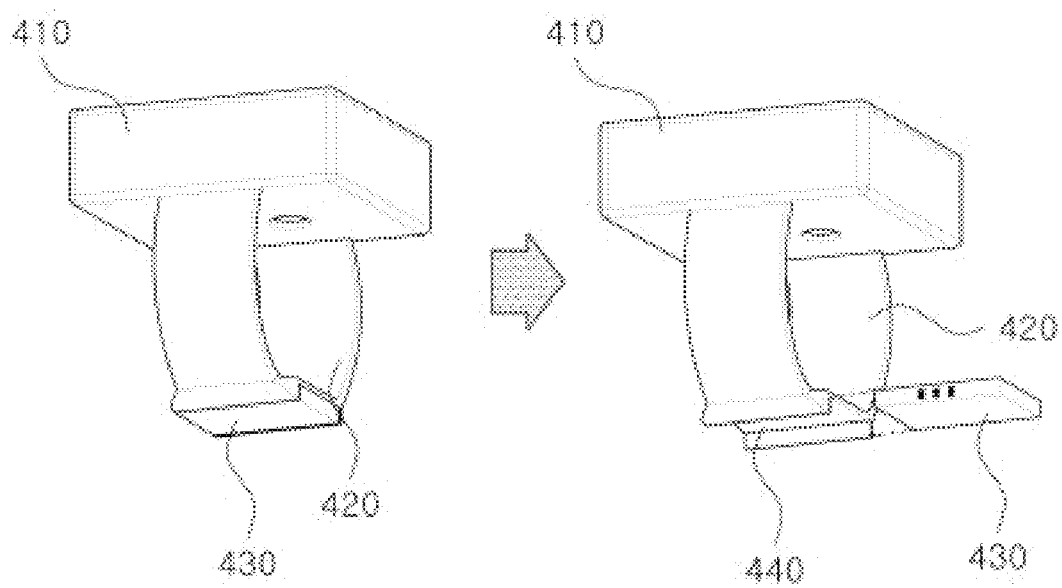
FIG. 8 is a conceptual diagram illustrating a band-type Raman signal analysis device.

FIG. 8 is a conceptual diagram illustrating a band-type continuous blood glucose measurement device.

The compact Raman spectroscopic analysis device 100 according to the present disclosure may be implemented in the form of a band that can be fixed to a wrist, ankle, forearm, or the like. To this end, the compact Raman spectroscopic analysis device 100 may include a housing 410 and a band 420.

The compact Raman spectroscopic analysis device 100 according to the present disclosure may further include a battery 430. The battery 430 may be disposed separately from the housing 410. For example, the battery 430 may be disposed across from the housing 410.

Further, a circuit that electrically connects components in the housing 410 to the battery 430 may be disposed within and through the band 420.

The battery 430 may be formed to be detachable from the band 420, and for this purpose, the band may include a battery coupling means 440. The battery coupling means 440 may secure the battery 430 to the band and also electrically connect the battery 430 to the circuit arranged within the band 420.

Further, an auxiliary battery may be provided within the housing 410. The auxiliary battery may ensure that the continuous blood glucose measurement device maintains its functionality without being interrupted while the battery 430 is replaced. By way of examples, the auxiliary battery may be implemented as a rechargeable battery, a coin cell, a capacitor, or the like. However, the type of auxiliary battery of the present disclosure is not limited thereto.

If the device is switched off when the battery is replaced, calibration may be necessary when restarting the blood sugar measurement after the battery replacement. This may result in an interruption in the blood sugar measurement, and the users may experience inconvenience of having to perform calibration every time the battery is replaced.

The subject matter of the present disclosure can improve user convenience by eliminating the need to turn off the device for replacing the battery.

Further, the processor 190 may be configured to obtain a Raman signal spectrum for each biomaterial by adjusting the rotation of the diffraction grating 129 and the width of the optical slit 127 while outputting light with different wavelengths for each biomaterial. Accordingly, the efficiency of obtaining the Raman signal spectrum can be improved.

The processor 190 may be configured to obtain a Raman signal spectrum for the first width of the slit for each biomaterial (such as glucose, protein, ketone, alcohol, caffeine, lactic acid, and fat), and may be configured to obtain a Raman signal spectrum of each biomaterial by decreasing the width of the slit. Accordingly, each biomaterial may be analyzed by setting the wavelength resolution of the Raman signal in various ways.

The processor 190 may be configured to cause the diffraction grating 129 to be rotated at a first rotation speed for each biological material to obtain a Raman signal spectrum, and then at speeds gradually slower than the first rotation speed to obtain a more precise Raman signal spectrum.

The processor 190 may be configured to set the position of the diffraction grating 129 and the width of the optical slit using the reference light source 116 prior to acquiring the Raman signal using the light source 111.

Further, the disclosed embodiments may be implemented in the form of a recording medium that stores instructions executable by a computer, controller, or processor. The instructions may be stored in the form of program codes or instructions, and when executed by a processor, may generate and/or operate program modules to perform the operations of the disclosed methods according to the embodiments of the present disclosure. The recording medium may be implemented as a non-transitory computer-readable recording medium.

Computer-readable storage media may include all types of storage media capable of storing instructions that can be deciphered by a computer. Examples include Read Only Memory (ROM), Random Access Memory (RAM), magnetic tape, magnetic disk, flash memory, and optical data storage devices.

As described above, embodiments have been described with reference to the attached drawings. Those skilled in the art to which the present disclosure pertains will understand that the present disclosure can be implemented in forms other than the disclosed embodiments without departing from the technical idea or essential features of the present disclosure. The disclosed embodiments are exemplary only and should not be construed as limiting.

What is claimed is:

1. A compact Raman spectroscopic analysis device, comprising:
   a housing that forms an internal accommodation space therein;
   a light source unit that is disposed within the housing and irradiates light onto a subject, wherein the light source unit includes a light source and a reference light source;
   a light receiving unit that is disposed within the housing and receives light reflected or scattered from the subject to obtain a Raman spectrum; and
   a processor that is disposed in the housing and configured to analyze biological material of the subject based on a peak area value of a Raman spectrum range corresponding to the biological material,
   wherein the light receiving unit comprises:
      a diffraction grating that reflects the reflected or scattered light;
      a slit through which the reflected light passes;
      an actuator for adjusting a width of the slit; and
      a light detector,
   wherein the diffraction grating is rotated by a driving unit to allow an amount of light and a wavelength band that reaches the light detector to be adjusted,
   wherein a reference position for rotational operation of the diffraction grating is established using the reference light source such that the reference position is set to a corresponding rotational position of the diffraction grating based on a signal of the reference light source incident on the diffraction grating, wherein the processor is configured to cause the actuator to adjust the width of the slit, wherein, prior to acquiring a Raman signal using the light source, the processor is configured to set a position of the diffraction grating and the width the slit using the reference light source, and wherein the processor is configured to:
cause the actuator to set the width of the slit to a first width to acquire a Raman signal spectrum; and
acquire the Raman signal spectrum of the biological material while decreasing the width of the slit so as to acquire the Raman signal with a plurality of wavelength resolutions.

2. The compact Raman spectroscopic analysis device of claim 1, wherein the driving unit comprises a motor, a worm gear system including a worm coupled to the motor and a worm wheel, and a holder disposed on an upper portion of the worm gear system, and
wherein the diffraction grating is disposed on an upper portion of the holder and configured to be rotated.

3. The compact Raman spectroscopic analysis device of claim 2, wherein the processor is configured to extract biological information of the subject based on a peak area value of a Raman spectrum range corresponding to at least one of glucose, protein, ketone, alcohol, caffeine, lactic acid, or fat.

4. The compact Raman spectroscopic analysis device of claim 3, wherein the processor is configured to, in response to the compact Raman spectroscopic analysis device starting operation or being worn on a user's body, perform calibration by controlling the light source unit and the light receiving unit.

5. The compact Raman spectroscopic analysis device of claim 4, wherein, when the calibration is performed, the processor is configured to:
control the light source unit to output the light at a predetermined intensity during a predetermined time period; and
set a light amount and an exposure time for the light source unit for measuring blood sugar based on a peak corresponding to a specific Raman transition value among the Raman spectrum acquired during the predetermined time period by the light receiving unit.

6. A Raman spectroscopic analysis method performed by a processor, comprising:
outputting, by a light source unit that is disposed in a housing that forms an internal accommodation space therein and includes a light source and a reference light source, light onto a subject;
obtaining, by a light receiving unit including a diffraction grating, a slit, an actuator for adjusting a width of the slit, and a light detector, a Raman signal of light reflected or scattered from the subject; and
analyzing, by the processor, biological information of the subject based on the Raman signal acquired by the light receiving unit,
wherein the diffraction grating is rotated by a driving unit to allow an amount of light and a wavelength band that reaches the light detector to be adjusted,
wherein a reference position for rotational operation of the diffraction grating is established using the reference light source such that the reference position is set to a corresponding rotational position of the diffraction grating based on a signal of the reference light source incident on the diffraction grating,
wherein the processor is configured to cause the actuator to adjust the width of the slit,
wherein, prior to acquiring a Raman signal using the light source, the processor is configured to set a position of the diffraction grating and the width the slit using the reference light source, and
wherein the processor is configured to:
cause the actuator to set the width of the slit to a first width to acquire a Raman signal spectrum; and
acquire the Raman signal spectrum of the biological material while decreasing the width of the slit so as to acquire the Raman signal with a plurality of wavelength resolutions.

7. The Raman spectroscopic analysis method of claim 6, wherein the driving unit comprises a motor, a worm gear system including a worm coupled to the motor and a worm wheel, and a holder disposed on an upper portion of the worm gear system, and
wherein the diffraction grating is disposed on an upper portion of the holder and configured to be rotated.

* * * * *